United States Patent [19]

Trottmann

[11] Patent Number: 5,550,217
[45] Date of Patent: Aug. 27, 1996

[54] AZO DYES

[75] Inventor: Martin Trottmann, Therwil, Switzerland

[73] Assignee: Ciba-Geigy Corporation, Tarrytown, N.Y.

[21] Appl. No.: 328,943

[22] Filed: Oct. 25, 1994

Related U.S. Application Data

[63] Continuation of Ser. No. 203,857, Feb. 28, 1994, abandoned, which is a continuation of Ser. No. 011,932, Feb. 1, 1993, abandoned.

[30] Foreign Application Priority Data

Feb. 3, 1992 [CH] Switzerland .................. 300/92

[51] Int. Cl.$^6$ ............................................. C09B 29/00
[52] U.S. Cl. ............................................. 534/732
[58] Field of Search ............................... 534/732

[56] References Cited

U.S. PATENT DOCUMENTS

| | | | |
|---|---|---|---|
| 2,373,700 | 4/1945 | McNally et al. | 260/205 |
| 3,166,074 | 1/1965 | Kurilla | 128/335.5 |
| 3,183,054 | 5/1965 | Fisher et al. | 8/94.33 |
| 3,888,625 | 6/1975 | Dawson et al. | 8/94.27 |
| 3,956,268 | 5/1976 | Altermatt | 534/732 |
| 4,030,881 | 5/1977 | Boyd | 8/39 |
| 4,042,580 | 8/1977 | Groebke | 534/732 |
| 4,221,711 | 9/1980 | Grund et al. | 534/732 |
| 5,071,443 | 12/1991 | Buhler | 8/639 |

FOREIGN PATENT DOCUMENTS 1521122  8/1978  United Kingdom.

OTHER PUBLICATIONS

Chemical Absract–vol. 100,#10, 69851d (1984).
Chemical Abstract–vol. 106,#16, 1213892 (1987).
Chemical Abstract–vol. 94,#10, 67273a (1981).
Chem. Abstracts–vol. 94, 67273a (1981) (Jap. Kokai, 80,116,754; 3/1979).

Primary Examiner—Johann Richter
Assistant Examiner—John Peabody
Attorney, Agent, or Firm—Kevin T. Mansfield

[57] ABSTRACT

Disperse dyes of formula

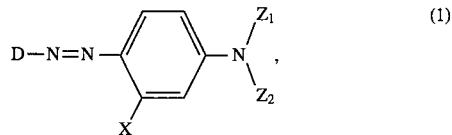
(1)

wherein
D is the radical of a diazo component of formula

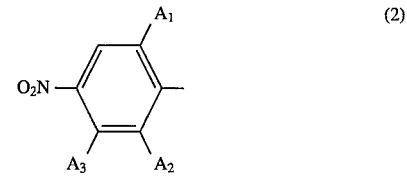
(2)

or

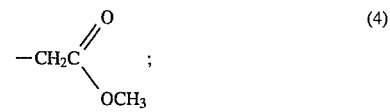
(3)

$Z_1$ is a radical of formula

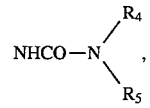
(4)

$Z_2$ is hydrogen or a radical of formula (4), X is hydrogen, halogen, $CF_3$, $R_3$, $OR_3$, $NH-CO-R_7$, $NH-CO-OR_8$, $NH-SO_2-R_7$ or

NHCO—N(R_4)(R_5), wherein $R_3$ is $C_1$–$C_6$alkyl; $R_4$ and $R_5$ are each independently of the other hydrogen, $C_1$–$C_4$alkyl or $C_1$–$C_4$alkoxy-$C_2$–$C_4$alkyl; $R_7$ is hydrogen, $C_1$–$C_6$alkyl, $C_1$–$C_4$alkoxy-$C_1$–$C_4$alkyl or phenyl; and $R_8$ is $C_1$–$C_6$alkyl or $C_1$–$C_4$alkoxy-$C_2$–$C_4$alkyl; $A_1$ is hydrogen, halogen, $SO_2R_3$, $CF_3$, $NO_2$ or CN; $A_2$ is hydrogen, halogen or CN; $A_3$ is hydrogen or halogen, with the proviso that at least one of the substituents X, $A_1$, $A_2$ and $A_3$ may not be hydrogen, and $A_4$ is hydrogen, halogen, nitro, $R_3$, $NHCOR_3$ or $OR_3$.

5 Claims, No Drawings

AZO DYES

This application is a continuation of application Ser. No. 08/203,857, filed on Feb. 28, 1994, now abandoned, which is a continuation of application Ser. No. 08/011,932, filed Feb. 1, 1993, now abandoned.

The present invention relates to disperse dyes, to their preparation and to the use thereof for dyeing textile materials.

Disperse dyes, i.e. dyes which are devoid of water-solubilising groups, have long been known in the art and are used for dyeing hydrophobic textile material. Often, however, the resultant dyeings are not fast to thermomigration. This problem occurs in particular with red to blue shades.

To eliminate this defect, special dyes have already been developed whose diffusion capacity is as low as possible owing to their molecular size and/or bulkiness. However, this characteristic often makes dyeing with such dyes difficult, as they cannot be used, or they have only very limited use, for dyeing by the exhaust process and, even in the thermosol process, they usually require undesirably high fixation temperatures.

It is an object of this invention to provide disperse dyes with which dyeings are obtained that are very fast to thermomigration and which nevertheless have a good build-up capacity in the exhaust and thermosol processes as well as in textile printing. The dyes are also suitable for discharge printing.

The dyes of this invention have the formula

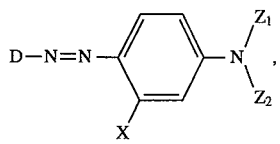    (1)

wherein

D is the radical of a diazo component of formula

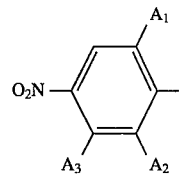    (2)

or

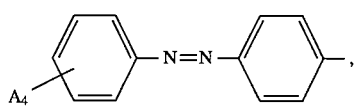    (3)

$Z_1$ is a radical of formula

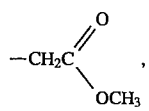    (4)

$Z_2$ is hydrogen or a radical of formula (4),

X is hydrogen, halogen, $CF_3$, $R_3$, $OR_3$, NH—CO—$R_7$, NH—CO—$OR_8$, NH—$SO_2$—$R_7$ or

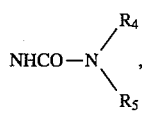

wherein $R_3$ is $C_1$–$C_6$alkyl, $R_4$ and $R_5$ are each independently of the other hydrogen, $C_1$–$C_4$alkyl or $C_1$–$C_4$alkoxy-$C_2$–$C_4$alkyl, $R_7$ is hydrogen, $C_1$–$C_6$alkyl, $C_1$–$C_4$alkoxy-$C_1$–$C_4$alkyl or phenyl and $R_8$ is $C_1$–$C_6$alkyl or $C_1$–$C_4$alkoxy-$C_2$–$C_4$alkyl, $A_1$ is hydrogen, halogen, $SO_2R_3$, $CF_3$, $NO_2$ or CN, $A_2$ is hydrogen, halogen or CN, $A_3$ is hydrogen or halogen, with the proviso that at least one of the substituents X, $A_1$, $A_2$ and $A_3$ may not be hydrogen, and $A_4$ is hydrogen, halogen, nitro, $R_3$, $NHCOR_3$ or $OR_3$.

Within the scope of this invention, alkyl will be generally understood as meaning straight chain, branched or cyclic alkyl groups. Typical examples of such groups are methyl, ethyl, propyl, isopropyl, butyl, isobutyl, tert-butyl, amyl, tert-amyl (1,1-dimethylpropyl), 1,1,3,3-tetramethylbutyl, hexyl, 1-methylpentyl, neopentyl, cyclopentyl, cyclohexyl, as well as the corresponding isomers. The alkyl groups preferably contain 1 to 6, more particularly 1 to 4, carbon atoms, unless otherwise specifically indicated.

Suitable alkoxy groups are preferably those containing 1 to 4 carbon atoms, typically methoxy, ethoxy, propoxy, isopropoxy, n-butoxy, isobutoxy or tert-butoxy.

Halogen will be generally understood as meaning fluoro, bromo or iodo and, preferably, chloro.

In especially useful dyes of formula (1) X is preferably hydrogen, $C_1$–$C_2$alkyl, $C_1$–$C_4$alkoxy, chloro, $C_1$–$C_4$alkylcarbonylamino, $C_1$–$C_4$alkoxycarbonylamino, $C_1$–$C_4$alkoxy-$C_1$–$C_4$alkylcarbonylamino, $C_1$–$C_4$-alkoxy-$C_2$–$C_4$alkoxycarbonylamino, $C_1$–$C_4$alkylsulfonylamino, or

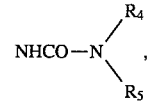

wherein $R_4$ and $R_5$ are each independently of the other hydrogen, $C_1$–$C_4$alkyl or $C_1$–$C_4$alkoxy-$C_2$–$C_4$alkyl.

Particularly preferred meanings of X are $C_1$–$C_2$alkyl, $C_1$–$C_4$alkylcarbonylamino, $C_1$–$C_4$alkoxycarbonylamino, $C_1$–$C_4$alkoxy-$C_1$–$C_4$alkylcarbonylamino or $C_1$–$C_4$ alkoxy-$C_2$–$C_4$ alkoxycarbonylamino.

In particularly useful compounds of formula (1), D is a radical of formula (2), wherein $A_1$ is preferably chloro, bromo, cyano, nitro, $CF_3$ or hydrogen, $A_2$ is hydrogen, chloro, bromo or cyano and $A_3$ is hydrogen. Among this group of compounds, particularly interesting compounds are those in which $A_1$ is chloro, cyano or nitro and $A_2$ is hydrogen, chloro, bromo or cyano.

$Z_1$ and $Z_2$ may be different from each other, but are preferably identical.

Owing to their good tinctorial properties, especially preferred dyes are those of formula

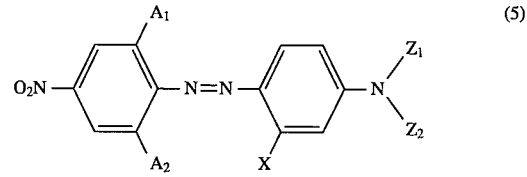    (5)

wherein $A_1$ is chloro, bromo, cyano, nitro, $CF_3$ or hydrogen, $A_2$ is hydrogen, chloro, bromo or cyano, X is hydrogen, $C_1$–$C_2$alkyl, $C_1$–$C_4$alkoxy, chloro, formylamino, $C_1$–$C_4$alkylcarbonylamino, $C_1$–$C_4$alkoxycarbonylamino, $C_1$–$C_4$alkoxy-$C_1$–$C_4$alkylcarbonylamino, $C_1$–$C_4$alkoxy-$C_2$–$C_4$alkoxycarbonylamino, $C_1$–$C_4$alkylsulfonylamino, or $$NHCO-N\begin{matrix} R_4 \\ \\ R_5 \end{matrix}$$

wherein $R_4$ and $R_5$ are each independently of the other hydrogen, $C_1$–$C_4$alkyl or $C_1$–$C_4$alkoxy-$C_2$–$C_4$alkyl, and $Z_1$ is a radical of formula $$-CH_2C\begin{matrix} O \\ \\ OCH_3 \end{matrix} \qquad (4)$$

and $Z_2$ is hydrogen or has the same meaning as $Z_1$.

Among this group of compounds, especially preferred compounds are those wherein $A_1$ is chloro, cyano or nitro, $A_2$ is hydrogen, chloro, bromo or cyano, X is $C_1$–$C_2$alkyl, $C_1$–$C_4$alkylcarbonylamino, $C_1$–$C_4$alkoxycarbonylamino, $C_1$–$C_4$alkoxy-$C_1$–$C_4$alkylcarbonylamino or $C_1$–$C_4$alkoxy-$C_2$–$C_4$alkoxycarbonylamino, $Z_1$ is $CH_2COOCH_3$, and $Z_2$ is hydrogen or $CH_2COOCH_3$.

The novel azo dyes of formula (1) can be prepared by methods which are known per se, conveniently by diazotising a compound of formula or and coupling the diazonium salt of this compound to a coupling component of formula wherein $A_1$, $A_2$, $A_3$, $A_4$, X, $Z_1$ and $Z_2$ are as defined for formula (1).

The diazotisation of the compounds of formula (6) or (7) is carried out in per se known manner, conveniently with sodium nitrite in acid, typically hydrochloric or sulfuric acid, aqueous medium. The diazotisation can, however, also be carried out with other diazotising agents, conveniently with nitrosylsulfuric acid. The reaction medium of the diaziotisation may contain an additional acid, typically phosphoric acid, sulfuric acid, acetic acid, propionic acid, hydrochloric acid or a mixture of these acids, for example a mixture of phosphoric acid and acetic acid. The diazotisation is conveniently carried out in the temperature range from –10° to +30° C., typically from –10° C. to room temperature.

The coupling of the diazotised compound of formula (6) or (7) to the coupling component of formula (8) is likewise carried out in known manner, conveniently in acid, aqueous or aqueous-organic medium, preferably in the temperature range from –10° to +30° C., most preferably below –10° C. Suitable acids include hydrochloric acid, acetic acid, sulfuric acid or phosphoric acid. Diazotisation and coupling may be carried out utilising a single vessel for diazotisation and coupling, i.e. in the same reaction medium.

The diazo components of formulae (6) and (7) are known or can be prepared in per se known manner.

Some of the coupling components of formula (8) are also known or they can be prepared in per se known manner.

A further object of the invention is the process for the preparation of coupling components of formula wherein $Z_3$ is a radical of formula —$CH_2$—$COOC_1$–$C_6$alkyl and $Z_4$ is hydrogen or $Z_3$, and $X_1$ is as defined for formula (9), which process comprises reacting an aniline of formula wherein $X_1$ is as defined for formula (9), with a $C_1$–$C_6$alkyl ester of a haloacetic acid, conveniently with methyl bromoacetate, methyl chloroacetate, ethyl bromoacetate, ethyl chloroacetate, propyl bromoacetate, propyl chloroacetate, n-butyl bromoacetate and n-butyl chloroacetate. This reaction is preferably carried out at elevated temperature, conveniently in the range from 60° to 120° C., in the presence of an acid acceptor such as sodium acetate or sodium carbonate, and in the presence or absence of an inert solvent.

The coupling components of formula are novel, wherein $X_1$ is halogen, $CF_3$, $R_3$, $OR_3$, NH—CO—$R_6$, NH—CO—$OR_3$, NH—$SO_2$—$R_6$ or

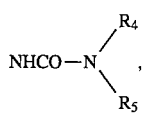

wherein $R_3$ is $C_1$–$C_6$alkyl, $R_4$ and $R_5$ are each independently of the other hydrogen, $C_1$–$C_4$alkyl or $C_1$–$C_4$alkoxy-$C_2$–$C_4$alkyl, and $R_6$ is $C_2$–$C_6$alkyl, $C_1$–$C_4$alkoxy-$C_1$–$C_4$alkyl or phenyl.

The coupling components of formula (9) constitute a further object of this invention. They are typically prepared by reacting an aniline of formula

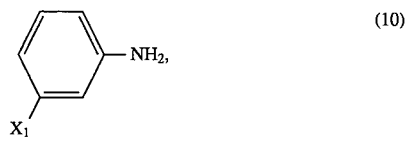 (10)

wherein $X_1$ is as defined for formula (9), with methyl bromoacetate. The reaction is preferably carried out as described above.

The novel compounds of formula (1) can be used as dyes for dyeing and printing semi-synthetic and, preferably, synthetic hydrophobic fibre materials, especially textile materials. Textile materials made from blends that contain such semi-synthetic or synthetic hydrophobic textile materials can also be dyed or printed with the novel compounds.

Semi-synthetic textile materials are in particular cellulose acetate and cellulose triacetate.

Synthetic hydrophobic textile materials consist primarily of linear aromatic polyesters, typically those from terephthalic acid and glycols, especially ethylene glycol, or condensates of terephthalic acid and 1,4-bis(hydroxymethyl)cyclohexane; from polycarbonates, typically those from α,α-dimethyl-4,4'-dihydroxydiphenylmethane and phosgene, or polyvinyl chloride and polyamide fibres.

The novel compounds are applied to the textile materials by known dyeing methods. Typically, polyester materials are dyed from an aqueous dispersion by the exhaust process in the presence of customary anionic or nonionic dispersants and in the presence or absence of customary swelling agents (carriers) in the temperature range from 80° to 140° C. Cellulose acetate is preferably dyed in the temperature from about 65° to 85° C., and cellulose triacetate in the temperature range up to 115° C.

The novel dyes do not stain wool and cotton simultaneously present in the dyebath or effect only minor staining (very good resist), so that they can also readily be used for dyeing polyester/wool and polyester/cellulose blends.

The novel dyes are suitable for dyeing by the thermosol process, for exhaust dyeing and for printing.

The textile material may be in any form of presentation, including fibres, thread, or nonwoven fabric, or as woven or knitted fabric.

It is expedient to convert the novel dyes, before use, into a dye formulation. This is done by milling the dye to an average particle size of 0.1 to 10 microns. Milling can be carried out in the presence of a dispersant. Typically, the dried dye is milled with a dispersant, or kneaded in paste form with a dispersant, and thereafter dried under vacuum or by spray drying. Printing pastes and dyebaths can be prepared by adding water to the formulations so obtained.

The customary thickeners will be used for printing. Typical examples of such thickeners are alginates, British gum, gum arabic, crystal gum, carob bean gum, tragacanth, carboxymethyl cellulose, hydroxyethyl cellulose, starch or synthetic products, including polyacrylamides, polyacrylic acid or copolymers thereof, or polyvinyl alcohols.

The cited materials, especially polyester material, are dyed with the novel dyes in level orange and red to blue shades having very good end-use properties, in particular good lightfastness and fastness to heat-setting, pleating and chlorine, and wetfastness properties such as fastness to water, perspiration and washing. The dyeings are also distinguished by very good rubfastness. The good fastness to thermomigration of the dyeings merits special mention.

The novel dyes can also be readily used for obtaining mixed shades in conjunction with other dyes. It is, of course, also possible to use mixtures of the novel dyes with one another.

In addition, the novel dyes are very suitable for dyeing hydrophobic textile material from supercritical $CO_2$.

Further objects of the invention are the aforementioned use of the azo dyes of formula (1) and a process for dyeing or printing semi-synthetic or synthetic hydrophobic material, preferably textile material, which comprises applying to, or incorporating in, said material one or more then one compound of formula (1). The hydrophobic fibre material is preferably polyester textile material. Further substrates which can be treated by the process of the invention and preferred process conditions have been discussed above in the more detailed description of the use of the compounds of formula (1).

The hydrophobic fibre material, preferably polyester textile material, dyed or printed by the instant process, also constitutes an object of the invention.

The novel dyes of formula (1) are also suitable for modern marking methods, for example heat transfer printing.

The invention is illustrated in more detail by the following non-limitative Examples in which, unless otherwise indicated, parts and percentages are by weight.

EXAMPLE 1

A mixture of 10.7 g of m-toluidine, 40 ml of methyl bromoacetate, 60 ml of methanol and 23.3 g of sodium carbonate is stirred for 8 hours at reflux temperature. The mixture is then cooled to room temperature and filtered. The filtrate is concentrated on a rotary evaporator and the residue is then distilled. At 136°–153° C./2 mbar 31 g of a yellow viscous oil of formula

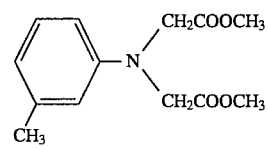

is obtained.

3.3 g of 2-cyano-4-nitroaniline are diazotised in known manner in concentrated sulfuric acid and the resultant diazonium salt is coupled at pH 3–5 to an equivalent amount of the above coupling component. The crude product obtained by filtration is taken up in 100 ml of methanol and, after stirring for 2 hours at reflux temperature, the product is isolated hot by filtration. This purification step is repeated. The product is dried, giving 6.1 g of crystals with a melting point of 192°–205° C. The dye has the formula

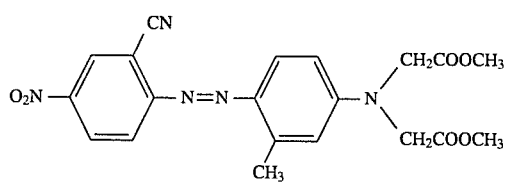

and dyes polyester textile material in a red shades. These dyeings have good fastness properties, in particular good fastness to thermomigration.

EXAMPLE 2

A mixture of 16.4 g of m-aminopropionanilide, 23.3 g of sodium carbonate and 50 ml of methyl chloroacetate is stirred for 9 hours at 100° C. After cooling to room temperature, the reaction mixture is diluted with 50 ml of acetone and filtered. Acetone and excess methyl chloroacetate are distilled from the filtrate, giving a brown oil which contains the two compounds of formulae

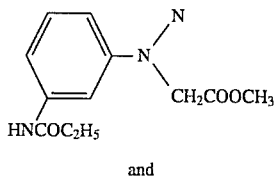

and

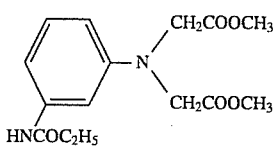

in the ratio of about 1:1.

The diazonium salt of 2-cyano-4-nitroaniline is coupled to the above described mixture of coupling components to give a mixture of dyes of formulae

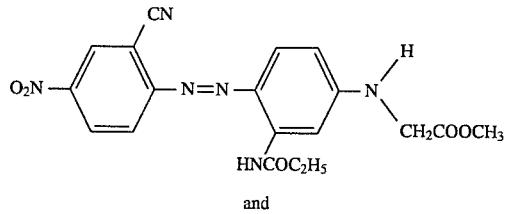

and

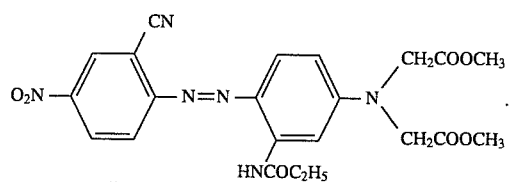

The mixture purified in methanol as described in Example 1 melts at 171°–189° C. and dyes polyester textile material in a red shade. The dyeings have good fastness properties, in particular good fastness to thermomigration.

EXAMPLE 3

A mixture of 15 g of m-aminoacetanilide, 11.5 g of sodium carbonate, 50 ml of methanol and 9.5 ml of methyl bromoacetate is stirred for 4 hours at 65° C. After cooling and filtration, the entire filter residue is recrystallised from 100 ml of water at pH 5. giving 16.5 g of colourless crystals of formula

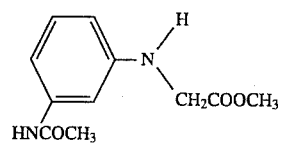

with a melting point of 108°–110° C.

This compound is coupled to the diazonium salt of 2-cyano-4-nitroaniline in the above described manner to give the dye of formula

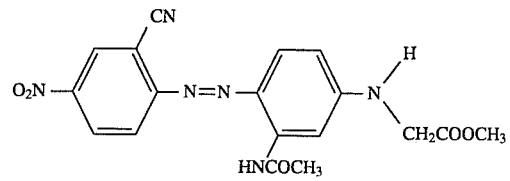

which dyes polyester textile material in a red shade. The dyeings have good fastness properties, in particular good fastness to thermomigration.

EXAMPLES 4–60

The following dyes can also be prepared in the manner described in Examples 1 to 3. They dye polyester textile material in the shades indicated in the second last column of Table 1.

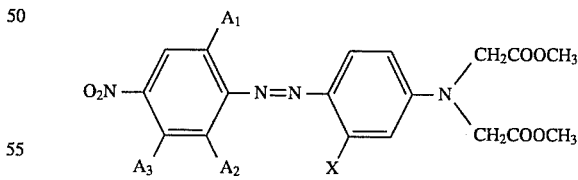

TABLE 1

| Ex. | $A_1$ | $A_2$ | $A_3$ | X | Shade | $\lambda_{max}$ (EtOH) |
|---|---|---|---|---|---|---|
| 4 | $NO_2$ | H | H | H | scarlet | 466 nm |
| 5 | CN | H | H | H | scarlet | 474 nm |
| 6 | $NO_2$ | Cl | H | H | reddish brown | 468 nm |
| 7 | CN | Br | H | H | reddish brown | 484 nm |
| 8 | Cl | H | H | $CH_3$ | brown | 458 nm |

TABLE 1-continued

| Ex. | A₁ | A₂ | A₃ | X | Shade | $\lambda_{max}$ (EtOH) |
|---|---|---|---|---|---|---|
| 9 | NO₂ | Br | H | CH₃ | claret | 488 nm |
| 10 | NO₂ | H | H | NHCOCH₃ | red | 500 nm |
| 11 | NO₂ | H | H | NHCOCH₂CH(CH₃)₂ | red | 510 nm |
| 12 | NO₂ | H | H | NHCOC₂H₅ | red | 502 nm |
| 13 | NO₂ | H | H | NHCOOC₂H₅ | red | 502 nm |
| 14 | CN | H | H | NHCOCH₃ | red | 508 nm |
| 15 | CN | H | H | NHCOOC₂H₅ | red | 506 nm |
| 16 | CN | H | H | NHCOC₂H₅ | red | 508 nm |
| 17 | Cl | H | H | NHCOCH₃ | scarlet | 486 nm |
| 18 | CF₃ | H | H | NHCOCH₃ | scarlet | 486 nm |
| 19 | NO₂ | CN | H | NHCOC₂H₅ | violet | 558 nm |
| 20 | CN | H | H | OCH₃ | red | 502 nm |
| 21 | Cl | H | H | NHCONH₂ | red | 500 nm |
| 22 | NO₂ | H | H | NHCO-phenyl | red | |
| 23 | CN | H | H | NHCONH₂ | red | 520 nm |
| 24 | NO₂ | Br | H | NHCONH₂ | ruby | |
| 25 | NO₂ | H | H | CH₃ | scarlet | 480 nm |
| 26 | CN | H | H | CF₃ | orange | 470 nm |
| 27 | Cl | H | H | OCH₃ | scarlet | 478 nm |
| 28 | CN | Br | H | NHCOCH₃ | violet | 542 nm |
| 29 | NO₂ | Br | H | Cl | brown | 464 nm |
| 30 | CN | H | H | NHCOH | red | |
| 31 | Cl | H | H | NHCOC₂H₅ | scarlet | 486 nm |
| 32 | H | H | H | NHCOCH₂OCH₃ | orange | 464 nm |
| 33 | CN | Cl | H | CH₃ | claret | 500 nm |
| 34 | NO₂ | Cl | H | CF₃ | brown | |
| 35 | SO₂CH₃ | Br | H | NHCOC₂H₅ | reddish brown | |
| 36 | NO₂ | H | H | NHCOOCH₃ | red | 502 nm |
| 37 | CN | H | H | NHCONHC₃H₇ | ruby | |
| 38 | H | H | H | NHCOCH₃ | orange | 464 nm |
| 39 | Cl | H | H | NHCON(CH₃)₂ | red | 502 nm |
| 40 | Cl | H | H | NHCONHC₂H₄OCH₃ | red | |
| 41 | CN | H | H | NHSO₂CH₃ | scarlet | 473 nm |
| 42 | H | H | H | NHCOC₂H₅ | orange | 468 nm |
| 43 | NO₂ | Cl | H | NHCOCH₃ | ruby | 518 nm |
| 44 | CN | H | H | NHCOOCH₃ | red | 506 nm |
| 45 | Cl | H | H | CF₃ | orange | 450 nm |
| 46 | NO₂ | H | Cl | NHCOCH₃ | ruby | |
| 47 | Br | BR | H | NHCOCH₃ | brown | |
| 48 | SO₂CH₃ | H | H | NHCOOC₂H₅ | brown | |
| 49 | CF₃ | Br | H | OCH₃ | brown | |
| 50 | Cl | Br | H | H | ochre | |
| 51 | SO₂CH₃ | H | H | OCH₃ | brown | |
| 52 | CN | CF₃ | H | NHCOCH₃ | ruby | |
| 53 | CF₃ | H | H | OCH₃ | scarlet | 472 nm |
| 54 | CF₃ | Br | H | CH₃ | brown | |
| 55 | NO₂ | H | Cl | CH₃ | ruby | |
| 56 | CN | H | H | NHCOOC₂H₄OCH₃ | red | 506 nm |
| 57 | Cl | H | H | NHCOCH₂OCH₃ | red | 484 nm |
| 58 | CN | CN | H | NHCOCH₃ | violet | 568 nm |
| 59 | CN | H | H | NHCOC₂H₄OC₂H₅ | red | 508 nm |
| 60 | Cl | Cl | H | Cl | ochre | 404 nm |

EXAMPLES 61–69

The following dyes can also be prepared in the manner described in Examples 1 to 3. They dye polyester textile material in the shades indicated in the second last column of Table 2.

TABLE 2

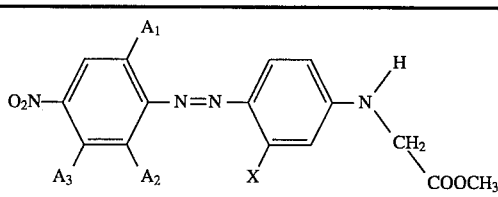

| Ex. | A₁ | A₂ | A₃ | X | Shade | $\lambda_{max}$ (EtOH) |
|---|---|---|---|---|---|---|
| 61 | Cl | Cl | H | Cl | ochre | 404 nm |
| 62 | Cl | H | H | NHCOCH₃ | scarlet | 500 nm |
| 63 | Cl | H | H | NHCONH₂ | red | 512 nm |
| 64 | CN | H | H | CH₃ | red | 490 nm |
| 65 | Cl | H | H | NHCONHC₃H₇ | red | |
| 66 | CN | H | H | NHCOCH₃ | red | 518 nm |

TABLE 2-continued

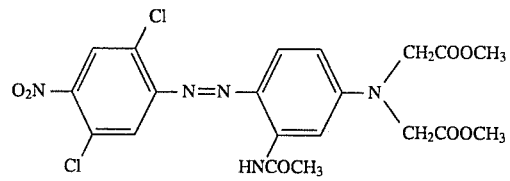

| Ex. | $A_1$ | $A_2$ | $A_3$ | X | Shade | $\lambda_{max}$ (EtOH) |
|---|---|---|---|---|---|---|
| 67 | CN | H | H | NHCOC$_2$H$_5$ | red | 516 nm |
| 68 | CN | H | H | CF$_3$ | scarlet | |
| 69 | NO$_2$ | NO$_2$ | Cl | OCH$_3$ | claret | 510 nm |

EXAMPLE 70

The diazonium salt of 4-aminoazobenzene is coupled to the compound of formula

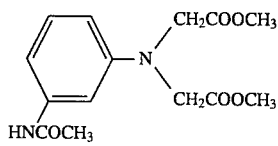

in the manner described in Example 1 to give the dye of formula

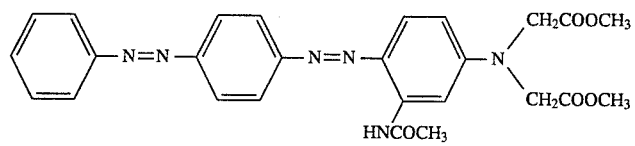

which dyes polyester textile material in an orange shade. The dyeings have good fastness properties, in particular good fastness to thermomigration. The following dyes can also be prepared in accordance with this Example. They dye polyester textile material in the shades indicated in the second last column of the Table 3.

TABLE 3

| Ex. | $A_4$ | X | Shade | $\lambda_{max}$ (EtOH) |
|---|---|---|---|---|
| 71 | H | H | orange | 436 nm |
| 72 | m-OCH$_3$ | CH$_3$ | orange | |
| 73 | m-NHCOC$_2$H$_5$ | H | orange | |
| 74 | p-NO$_2$ | OCH$_3$ | orange | |

EXAMPLE 75

The diazonium salt of 2,5-dichloro-4-nitroaniline is coupled by the method described in Example 1 to the coupling component used in Example 70 to give the dye of formula which dyes polyester textile material in a scarlet shade. The dyeings have good fastness properties, in particular good fastness to thermomigration.

EXAMPLE 76

1 g of the dye described in Example 1, 17 g of water and 2 g of a commercial dispersant of the dinaphthylmethane disulfonate type are milled in a sand mill and converted into a 5% dispersion.

A 0.5% dyeing (based on pigment and substrate) is produced with this formulation on polyester fabric by the exhaust process at 130° C. and given a reductive afterclear. The red dyeing so obtained has very good end-use properties and, in particular, excellent fastness to thermomigration.

Very good fastness properties can also be achieved by dyeing a polyester/cotton blend (67:33) by the thermsol process (10 g/l of dye, pick-up 50%, setting temperature 210° C.).

To test the fastness to thermomigration, the dyed material is treated with a a textile softener of the distearyl diethylenetriamine type and then heated for 30 seconds to 180° C. The rubfastness and washfastness (60° C.) of the sample are then tested.

EXAMPLE 77

A mixture of 50 g of 3-aminoacetanilide, 180 g of methyl chloroacetate, 48 g of sodium carbonate and 6 g of sodium bromide is heated to 115° C. with evolution of CO$_2$ and stirred for 10 hours at this temperature. The water of reaction is distilled continuously from the reactor as an azeotropic mixture (boiling point 95° C.) with methyl chloroacetate. After cooling, the organic phase is washed with 250 ml of water and subsequently distilled under reduced pressure to leave, as residue, 98 g of the compound of formula

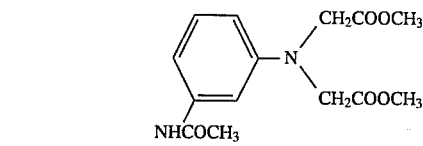

in the form of a brown oil which solidifies upon cooling to room temperature.

In accordance with the general procedure described in Example 77, the following compounds of formula

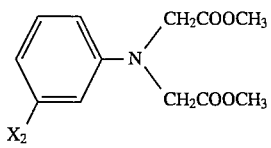

listed in Table 4 are prepared.

TABLE 4

| $X_2$ | Reaction time | Appearance of the crude product at room temperature | mp ($CH_3OH$) |
|---|---|---|---|
| $NHCOOC_2H_5$ | 15 h | oil | |
| $NHCOC_2H_5$ | 10 h | crystalline | 104–110° C. |
| $NHCOCH_2OCH_3$ | 15 h | crystalline | 96–100° C. |
| $OCH_3$ | 16 h | oil | |
| $NHSO_2CH_3$ | 20 h | oil | |
| $CF_3$ | 90 h | oil | |

EXAMPLE 78

A mixture of 50 g of 3-aminoacetanilide, 180 g of methyl chloroacetate, 34 g of lithium carbonate and 5 g of lithium bromide is heated to 115° C. with evolution of $CO_2$ and stirred for 8 hours at this temperature. The water of reaction is distilled continuously from the reactor as an azeotropic mixture (boiling point 95° C.) with methyl chloroacetate. After cooling, the organic phase is washed with 250 ml of water and subsequently distilled under reduced pressure to leave, as residue, 87 g of the compound of formula

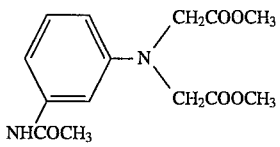

in the form of a brown oil which solidifies upon cooling to room temperature.

EXAMPLE 79

A mixture of 50 g of 3-aminoacetanilide, 180 g of methyl chloroacetate, 62 g of potassium carbonate and 7 g of potassium bromide is heated to 115° C. with evolution of $CO_2$ and stirred for 8 hours at this temperature. The water of reaction is distilled continuously from the reactor as an azeotropic mixture (boiling point 95° C.) with methyl chloroacetate. After cooling, the organic phase is washed with 250 ml of water and subsequently distilled under reduced pressure to leave as residue, the compound of formula

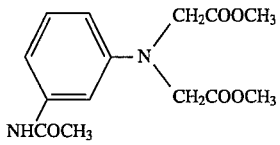

in the form of a brown oil which solidifies upon cooling to room temperature.

EXAMPLE 80

A mixture of 50 g of 3-aminoacetanilide, 180 g of methyl chloroacetate, 48 g of sodium carbonate and 9 g of methyl bromoacetate is heated to 115° C. with evolution of $CO_2$ and stirred for 10 hours at this temperature. The water of reaction is distilled continuously from the reactor as an azeotropic mixture (boiling point 95° C.) with methyl chloroacetate. After cooling, the organic phase is washed with 250 ml of water and subsequently distilled under reduced pressure to leave, as residue, the compound of formula

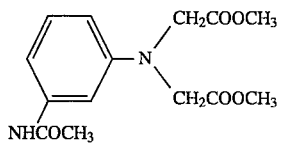

in the form of a brown oil which solidifies upon cooling to room temperature.

EXAMPLE 81

A mixture of 50 g of 3-aminoacetanilide, 180 g of methyl chloroacetate, 48 g of sodium carbonate and 1 g of potassium iodide is heated to 100° C. with evolution of $CO_2$ and stirred for 8 hours at this temperature. The water of reaction is distilled continuously from the reactor as an azeotropic mixture (boiling point 95° C.) with methyl chloroacetate. After cooling, the organic phase is washed with 250 ml of water and subsequently distilled under reduced pressure to leave, as residue, the compound of formula

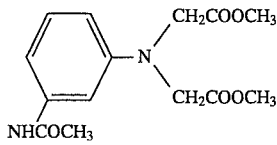

in the form of a brown oil which solidifies upon cooling to room temperature.

EXAMPLE 82

A mixture of 50 g of 3-aminoacetanilide, 180 g of methyl chloroacetate, 48 g of sodium carbonate and 6 g of sodium bromide is heated to 115° C. with evolution of $CO_2$ and stirred for 4 hours at this temperature. The water of reaction is distilled continuously from the reactor as an azeotropic mixture (boiling point 95° C.) with methyl chloroacetate. After cooling, the organic phase is washed with 250 ml of water and subsequently distilled under reduced pressure to leave, as residue, a mixture of the compounds of formulae

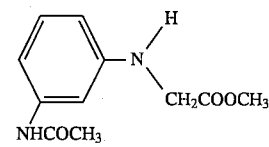

and

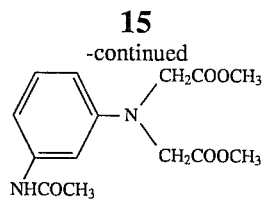

in the ratio 40:40.

What is claimed is:

1. A dye of the formula

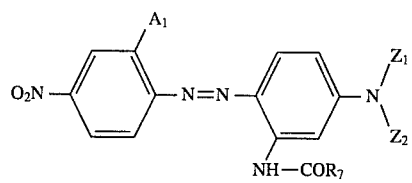

wherein $A_1$ is chloro or cyano, $R_7$ is $C_1$–$C_6$alkyl, $Z_1$ is a radical of formula

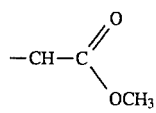

and $Z_2$ is hydrogen or a radical of formula (4).

2. A dye according to claim 1 of the formula

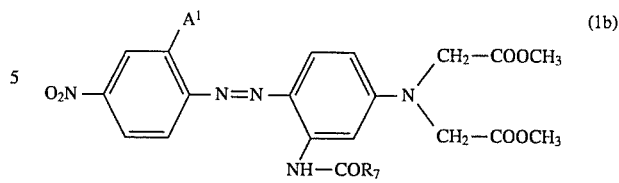

wherein $A_1$ is chloro or cyano and $R_7$ is $C_1$–$C_6$alkyl.

3. A dye according to claim 1 of the formula

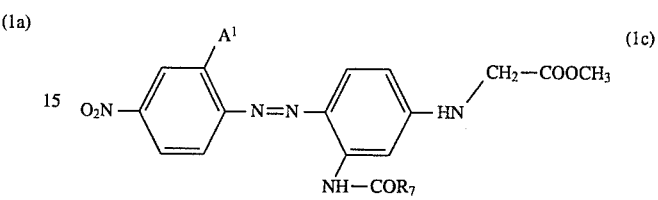

wherein $A_1$ is chloro or cyano and $R_7$ is $C_1$–$C_6$alkyl.

4. A dye according to claim 2, wherein $A_1$ is chloro and $R_7$ is methyl.

5. A dye according to claim 2, wherein $A_1$ is cyano and $R_7$ is methyl.

* * * * *